United States Patent [19]

Lentz et al.

[11] Patent Number: 4,798,911
[45] Date of Patent: Jan. 17, 1989

[54] CATALYST COMPOSITION AND METHOD FOR SELECTIVE DEHYDROGENATION

[75] Inventors: Carl M. Lentz, Mt. Carmel; Bruce L. Gustafson; Paul S. Wehner, both of Kingsport, all of Tenn.

[73] Assignee: Eastman Kodak Company, Rochester, N.Y.

[21] Appl. No.: 75,375

[22] Filed: Jul. 20, 1987

[51] Int. Cl.$^4$ .................. C07C 37/06; C07C 39/12; C07C 5/333; C07C 5/367
[52] U.S. Cl. .................. 568/747; 568/744; 568/772; 585/660
[58] Field of Search ............... 568/772, 799, 589, 626, 568/743, 744, 747; 585/660

[56] References Cited

U.S. PATENT DOCUMENTS

| | | | |
|---|---|---|---|
| 3,592,867 | 7/1971 | Pollitzer | 585/660 |
| 3,801,651 | 4/1975 | Adolphen | 568/799 |
| 3,953,526 | 4/1975 | Rosenthal | 568/772 |
| 4,024,196 | 5/1975 | Krekeler | 568/772 |
| 4,060,559 | 11/1977 | Goto et al. | 568/747 |
| 4,088,702 | 5/1978 | Goto et al. | 568/747 |
| 4,154,965 | 5/1979 | Meijer et al. | 568/772 |
| 4,160,113 | 7/1979 | Muller et al. | 568/772 |
| 4,319,054 | 3/1982 | Maki et al. | 568/799 |
| 4,419,529 | 12/1983 | Steinmetz | 568/799 |
| 4,431,848 | 2/1984 | Crew | 585/660 |

*Primary Examiner*—Werren B. Lone
*Attorney, Agent, or Firm*—S. E. Reiter; William P. Heath, Jr.

[57] ABSTRACT

A method for selective dehydrogenation of a compound, comprising contacting a compound of the formula

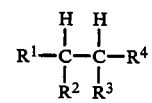

wherein each $R^1$, $R^2$, $R^3$ and $R^4$ is independently selected from the group consisting of H, ($C_1$–$C_{20}$) alkyl, ($C_3$–$C_{20}$) cycloalkyl, ($C_6$–$C_{20}$) aryl, ($C_7$–$C_{20}$) alkylaryl, ($C_7$–$C_{20}$) aralkyl groups, as well as substituted ($C_1$–$C_{20}$) alkyl, ($C_3$–$C_{20}$) cycloalkyl, ($C_6$–$C_{20}$) aryl, ($C_7$–$C_{20}$) aralkyl and ($C_7$–$C_{20}$) arylalkyl moieties, optionally further substituted with —OR, wherein R is $R^1$, $R^2$, $R^3$ or $R^4$; and wherein $R^1$ and $R^2$ or $R^3$ and $R^4$ may be joined as part of a ring structure, at a dehydrogenation temperature in the presence of a catalyst comprising about 0.01 wt %–19.9 wt % Pd and about 0.01 wt %–19.9 wt % Cu on a carbon support, wherein the total amount of (Pd+Cu) on the support is about 0.02 wt % to 20 wt %, the weight ratio of Pd:Cu is about 1:1 to 10:1, and the carbon support has a surface area of at least about 100 m$^2$/g and is essentially free of reactive sulfur.

A selective dehydrogenation catalyst having the composition described supra is disclosed as is a method of preparing the same. This catalyst is highly selective for dehydrogenating a variety of substrates while minimizing the formation of unwanted hydrogenolysis by-products.

23 Claims, No Drawings

CATALYST COMPOSITION AND METHOD FOR SELECTIVE DEHYDROGENATION

DESCRIPTION

This invention relates to a catalyst composition which has been shown to be useful for the selective catalytic dehydrogenation of a variety of organic substrates.

BACKGROUND OF THE INVENTION

Dehydrogenation reactions have been used to effect aromatization as well as to place an olefinic linkage in an open chain system (see, P. A. Plattner, in "Newer Methods of Preparative Organic Chemistry", Wiley Intersciences, New York, pp. 21–59 (1948); Chem. Rev. 78: 317–361 (1978)). Two types of reagents are most frequently used to effect aromatization: (a) hydrogenation catalysts such as platinum, palladium, nickel, etc., and (b) sulfur or selenium which combine with the hydrogen evolved to give $H_2S$ or $H_2Se$.

Other reagents have also been used for dehydrogenation, e.g., atmospheric oxygen, selenium dioxide, quinones (see, Jackman, L. M., Org. Chem. 2: 329–366 (1960)) and activated charcoal (see, Shuikin and Naryschkina, J. Prakt. Chem. [4] 13: 183 (1961).

Dehydrogenation of open-chain systems to give a double bond in a specific location is not usually a feasible process, though industrially mixtures of olefins are obtained in this way from alkanes.

There are few highly selective methods for catalytic dehydrogenation. Competing secondary reactions such as hydrogenolysis of carbon-oxygen bonds may occur detracting from the synthetic utility of this approach. For example, during the catalytic dehydrogenation of cyclohexylhydroquinone to phenylhydroquinone using a supported palladium catalyst, large amounts of hydrogenolysis by-products such as 2- and 3-phenyl phenols are produced.

Thus, it is apparent there is still a need for a catalyst that will effect a selective dehydrogenation of substrates that are susceptible to hydrogenolysis.

SUMMARY OF THE INVENTION

A catalyst composition has now been discovered that can be used for the selective dehydrogenation of a variety of substrates. A unique feature of this catalyst is the high degree of selectivity obtained thus avoiding the formation of unwanted reaction by-products.

The catalyst composition of the invention comprises about 0.01–19.9 wt % Pd, and
about 0.01–19.9 wt % Cu,
on a carbon support, wherein the total amount of (Pd+Cu) on the support is about 0.02 wt % to 20 wt %, the weight ratio of Pd:Cu is about 1:1 to 10:1 and the carbon support has a surface area of at least about 100 m²/g and is essentially free of reactive sulfur.

The catalyst of the invention is prepared by a method comprising
heat-treating a carbon support having a surface area of at least about 100 m²/g at a temperature and for a time sufficient to remove essentially all volatile sulfur therefrom;
contacting the heat-treated carbon support with at least one Pd- source selected from the group consisting of palladium and anion-containing compounds of palladium and at least one Cu- source selected from the group consisting of copper and anion-containing compounds of copper in amounts effective to attain on the support a final amount of 0.01–19.9 wt % Pd and 0.01–19.9 wt % Cu, a total amount of (Pd+Cu) of about 0.02 wt % to 20 wt %, and a weight ratio of Pd:Cu of about 1:1 to 10:1. The catalyst is calcined prior to use under conditions effective to decompose the Pd- and Cu-containing compounds employed for catalyst preparation. Preferably, calcination will be carried out under conditions effective to remove substantially all the anions of the Pd- and Cu-containing compounds but not sufficient to cause excessive combustion of the carbon support.

This invention also relates to a method of dehydrogenating a compound, comprising
contacting a compound of the formula

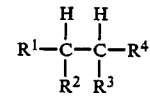

wherein each $R^1$, $R^2$, $R^3$ and $R^4$ is independently selected from the group consisting of
H, ($C_1$–$C_{20}$) alkyl, ($C_3$–$C_{20}$) cycloalkyl, ($C_6$–$C_{20}$) aryl, ($C_7$–$C_{20}$) alkylaryl, and ($C_6$–$C_{20}$) arylalkyl groups, as well as substituted ($C_1$–$C_{20}$) alkyl, ($C_3$–$C_{20}$) cycloalkyl, ($C_6$–$C_{20}$) aryl, ($C_7$–$C_{20}$) alkylaryl and ($C_6$–$C_{20}$) arylalkyl groups; each such group optionally further substituted with —OR, wherein R is $R^1$, $R^2$, $R^3$ or $R^4$; and wherein $R^1$ and $R^2$ or $R^3$ and $R^4$ may be joined as part of a ring structure,
under dehydrogenation conditions in the presence of a catalyst comprising about 0.01 wt %–19.9 wt % Pd, and about 0.01 wt %–19.9 wt % Cu on a carbon support, wherein the total amount of (Pd+Cu) on the support is about 0.02 wt % to 20 wt %, the weight ratio of Pd:Cu is about 1:1 to 10:1 and the carbon support has a surface area of at least about 100 m²/g and is essentially free of reactive sulfur.

When palladium supported on an inert support in the absence of any amounts of copper is utilized as a dehydrogenation catalyst, large amounts of hydrogenolysis by-products are obtained. One such example is the dehydrogenation of cyclohexylhydroquinone in which by-products such as 2- and 3-hydroxybiphenyls are evolved.

On the other hand, when the dehydrogenation reaction is conducted utilizing the catalyst of this invention a selective dehydrogenation occurs and substantially no by-products are produced. Thus, when cyclohexylhydroquinone is dehydrogenated according to the inventive method it yields phenylhydroquinone substantially in the absence of hydrogenolysis biphenyl by-products (see Example 1).

Other objects, advantages and features of the present invention will become apparent to those skilled in the art from the following discussion and appended claims.

DETAILED DESCRIPTION OF THE INVENTION

The dehydrogenation method of the present invention is conducted with the aid of a mixed metal catalyst composition comprising palladium and copper supported on a carbon support.

The catalyst composition of the invention comprises
about 0.01–19.9 wt % Pd, and
about 0.01–19.9 wt % Cu, on a carbon support, wherein the total amount of (Pd +Cu) on the support is about 0.02 wt % to 20 wt %, the weight ratio of Pd:Cu is about 1:1 to 10:1 and the carbon support has a surface area of at least about 100 m²/g and is essentially free of reactive sulfur.

A preferred catalyst composition comprises about 5 wt % to 8 wt % of palladium and about 0.5 wt % to 2.5 wt % of copper on carbon. An extremely efficient, and thus a most preferred, catalyst is attained when a palladium:copper ratio is utilized which is between about 3.0:1 and 4.0:1.

The catalyst composition of the invention is prepared by the method described supra. The contacting of the carbon support with the Pd- and Cu-containing compounds may be conducted by techniques which are standard in the art, such as for example, aggregation, precipitation onto a support, evaporation of a metal-containing solution onto a support and the like. By means of example, the catalyst of the invention is prepared by dissolving appropriate amounts of at least one palladium- and anion-containing compound and at least one Cu- and anion-containing compound in a solvent, the amounts being sufficient to attain a desired metal loading on a carbon support and the solution is added to the carbon support material which has been heated to remove any volatile sulfur content at, e.g., about 700° C.–900° C. The solvent may be water, although the use of other solvents is also contemplated. Any excess solvent may be removed by methods known in the art, and the sample is then dried. The catalyst is then calcined prior to use to remove any anions present.

The Pd- and Cu-containing compounds employed for catalyst preparationl are compounds where the metals are associated with the anion. Any anion which may be removed by calcination or does not detract from the activity of the finished catalyst is suitable for the preparation of the present catalyst.

In accordance with another embodiment of the present invention, a method is provided for dehydrogenating compounds of the formula

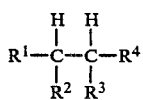

wherein each $R^1$, $R_2$, $R^3$ and $R^4$ is independently selected from the group consisting of H, $(C_1-C_{20})$ alkyl, $(C_3-C_{20})$ cycloalkyl, $(C_6-C_{20})$ aryl, $(C_7-C_{20})$ alkylaryl, and $(C_7-C_{20})$ arylalkyl groups, as well as substituted $(C_1-C_{20})$ alkyl, $(C_3-C_{20})$ cycloalkyl, $(C_6-C_{20})$ aryl, $(C_7-C_{20})$ alkylaryl and $(C_6-C_{20})$ arylalkyl groups; each such group optionally substituted with —OR, wherein R is $R^1$, $R^2$, $R^3$ or $R^4$; and wherein $R^1$ and $R^2$ or $R^3$ and $R^4$ may be joined as part of a ring structure.

A number of classes of compounds fall within this broad definition, e.g., straight chain alkanes having 2 up to 20 carbon atoms, branched chain alkanes having 4 up to 20 carbon atoms, alkaryl compounds such as, for example, compounds of the formula:

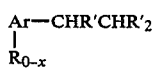

wherein each R is independently selected from the group consisting of
—OZ, wherein Z=H,
$C_1-C_{20}$ alkyl,
$C_3-C_{20}$ cycloalkyl,
$C_4-C_{20}$ aromatic or heteroaromatic moiety,

wherein $R^1 = C_1-C_{20}$ alkyl, or $C_3-C_{20}$ cycloalkyl;

wherein Y=H
$C_1-C_{20}$ alkyl, or
$C_3-C_{20}$ cycloalkyl;

wherein Y is as defined above,
—$SO_yZ'$, wherein
$Z'$ is
$C_1-C_{20}$ alkyl or
$C_2-C_{20}$ cycloalkyl;
and y=1 or 2;
wherein each R' is independently H, $C_1-C_{20}$ alkyl, $C_3-C_{20}$ cycloalkyl, $C_4-C_{20}$ aromatic or heteroaromatic moiety; wherein Ar is an aromatic moiety having 6 up to 14 carbon atoms; wherein x is 4 when Ar has 6 carbons, x is 6 when Ar has 10 carbons and x is 8 when Ar is 14; and diaryl ethanes of the formula:

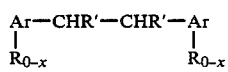

wherein each R is independently selected from the group consisting of
—OZ, wherein Z=H,
$C_1-C_{20}$ alkyl,
$C_3-C_{20}$ cycloalkyl, or
$C_4-C_{20}$ aromatic or heteroaromatic moiety;

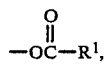

wherein $R^1 = C_1-C_{20}$ alkyl, or $C_3-C_{20}$ cycloalkyl;

wherein Y=H,
$C_1-C_{20}$ alkyl, or
$C_3-C_{20}$ cycloalkyl;

wherein Y is as defined above,
—$SO_yZ'$, wherein
$Z'$ is $C_1-C_{20}$ alkyl or $C_2-C_{20}$ cycloalkyl;
and y=1 or 2;
wherein each R' is independently H, $C_1-C_{20}$ alkyl, $C_3-C_{20}$ cycloalkyl, $C_4-C_{20}$ aromatic or heteroaromatic moiety; wherein Ar is an aromatic moiety having 6 up to 14 carbon atoms; wherein x is 4 when Ar has 6 carbons, x is 6 when Ar has 10 carbons and x is 8 when Ar is 14; as well as phenols, hydroquinones of the structure:

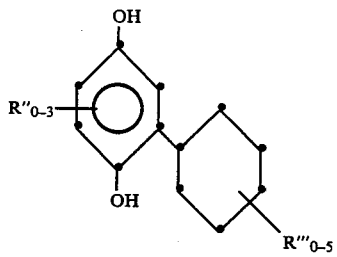

wherein each R″ is independently $C_1$–$C_{20}$ alkyl, $C_3$–$C_{20}$ cycloalkyl, $C_4$–$C_{20}$ aromatic or heteroaromatic moiety; and wherein each R‴ is independently
$C_1C_{20}$ alkyl,
$C_3$–$C_{20}$ cycloalkyl,
$C_6$–$C_{12}$ aryl,
$C_7$–$C_{20}$ aralkyl or alkaryl,
—OZ, wherein Z=H,
  $C_1$–$C_{20}$ alkyl,
  $C_3$–$C_{20}$ cycloalkyl,
  $C_4$–$C_{20}$ aromatic or heteroaromatic moiety,

wherein R′=$C_1$–$C_{20}$ alkyl, or $C_3$–$C_{20}$ cycloalkyl;

wherein Y=H,
$C_1$–$C_{20}$ alkyl, or
$C_3$–$C_{20}$ cycloalkyl;

wherein Y is as defined above,
—$SO_yZ'$, wherein
Z is $C_1$–$C_{20}$ alkyl, or $C_3$–$C_{20}$ cycloalkyl;
and y=1 or 2.
and the like.

Exemplary compounds which are included in the scope of dehydrogenatable compounds include cyclohexylhydroquinone and substituted derivatives thereof, 1,2-diphenylethane and substituted derivatives thereof, ethylbenzene and substituted derivatives thereof, alkanes such as propane, butane, pentane, hexane, heptane, octane, nonane and decane.

The dehydrogenation reaction according to the present method is preferably conducted at a temperature ranging from between about 100° C. to 400° C. A still more preferred range of temperatures is between about 150° C. and 300° C. The reaction is preferably conducted at atmospheric pressure, although other pressures are also contemplated herein.

The dehydrogenation reaction of the present method may be conducted in either a fixed bed or a slurry reactor. When the reaction is conducted in a slurry reactor, the catalyst utilized in the present method may be recycled from the slurry by filtering the hot reaction mixture. The filtration may be conducted at the reaction temperature, above the melting point of the reaction mixture or at a temperature between 100° C. and 200° C. A preferred range of temperatures for recovering the catalyst by filtration is between about 125° C. and 150° C.

In a preferred embodiment of the invention, hydrogen gas produced as a result of the reaction is removed from the reaction atmosphere as the reaction proceeds. This can be accomplished by a variety of techniques as are well known by those of skill in the art. For example, the removal of hydrogen gas can be attained by circulating an inert gas through the atmosphere immediately above, or directly into, the reaction mixture. By means of example, the inert gas may be nitrogen. However, other unreactive gases may also be utilized for the removal of the hydrogen gas. As one alternative, hydrogen gas can be removed by careful addition of a purge gas containing small amounts of oxygen, which enables the removal of hydrogen as water.

The net result of hydrogen gas removal is to shift the equilibrium concentration from the starting material or substrate to the product of the reaction by removing from the system any amount of hydrogen produced.

The selective dehydrogenation reaction of this invention may be conducted for a period of time which varies with the substrate, desired percent conversion to product, mode of operation, etc. The time may vary in the range of about 1 minute up to 32 hours. In a fixed bed reactor, for example, reaction times of one minute or less may be suitable to achieve acceptable conversion levels, while in slurry or stirred tank reactors, reaction times of several hours or more may be required to achieve acceptable conversion levels. It is recognized, of course, that an artisan may, without undue experimentation, adjust the period of time for the reaction to proceed by following the progress of the reaction under specific conditions. The progress of the reaction may be monitored by appropriate known analytical techniques, e.g., by extracting aliquots from the reaction mixture at different times for analysis by gas chromatography.

The selective dehydrogenation reaction of this invention may be optionally conducted in the presence of a solvent. Suitable solvents for use with the present method are solvents which are stable under reaction conditions. Examples of suitable solvents are biphenyl, naphthalene, diphenylether, tetralin, durene, prehnitene or 1,2,3,4-tetramethylbenzene, and the like.

When the dehydrogenation reaction is completed, the dehydrogenated product may be isolated from the reaction mixture (including the catalyst), and then further purified, by employing any of a variety of techniques readily available to those of skill in the art, e.g., by filtration, distillation, and the like.

Having now generally described this invention, the same will be better understood by reference to the following examples, which are included herein for purposes of illustration only, and are not intended to be limiting of the invention or any embodiment thereof.

EXAMPLES

Catalyst employed in the examples which follow was prepared according to the general procedure set forth below:

A carbon support material is heated to remove any residual volatile sulfur content. This is done at 700°–900° C. (in a hydrogen flow) for eight hours prior to metal addition. Appropriate amounts of palladium and copper nitrates necessary to achieve the desired metal loading are dissolved in water and the resulting solution added to the carbon support. Excess solvent is then removed by heating at 90° C. in air for several hours. Once the sample is dry, the materials are calcined in flowing air (i.e., a gas hourly space velocity (GHSV) in excess of about 1000/hr.) at 350° C. for four hours prior to use.

EXAMPLE 1

Dehydrogenation of Cyclohexylhydroquinone According to the Prior Art and the Invention Method The following is a small scale reaction which is representative of the invention method, which can also be successfully conducted on a large scale.

A 250-ml 3-neck flask was fitted with a tube for the subsurface addition of gas, a mechanical stirrer, a thermometer and a condenser.

A sample for Test I was prepared by adding to the flask 100 g biphenyl, 20 g cyclohexylhydroquinone and 2.0 g of a catalyst containing 5 wt % Pd, 1.5 wt % Cu on carbon; then the flask was heated to 250° C. During the course of the reaction, nitrogen gas was incorporated into the reaction atmosphere by subsurface addition thereof. After stirring the mixture for 24 hours at 250° C., an aliquot of the reaction mixture was analyzed by gas chromatography and found to contain 85% phenylhydroquinone and 10% cyclohexylhydroquinone as well as 3.2% hydrogenolysis by-products. This experiment is representative of the invention method.

The same procedure was conducted in the presence of 5% Pd on carbon but without copper (test II). The reaction mixture was found to contain 90% hydrogenolysis by-products and only 10% phenylhydroquinone. This experiment is representative of the prior art.

The results of these tests are summarized in Table 1.

TABLE 1
Dehydrogenation Method Using Prior Art and Invention Catalyst

| | | | Products Obtained | | |
|---|---|---|---|---|---|
| Dehydrogenation Catalyst | | | Cyclohexyl-hydro-quinone | Phenyl-hydro-quinone | Hydro-genolysis by-products |
| Test | Pd | Cu | Carbon | | | |
| I | Yes | Yes | Yes | 10% | 85% | 3.2% |
| II | Yes | No | Yes | — | 10% | 90% |

The above results indicate the superiority (high selectivity for dehydrogenation) of the invention method conducted with a catalyst containing palladium and copper on a carbon support (Test I) when compared with the prior art method conducted with a catalyst containing only palladium on a carbon support (Test II).

EXAMPLE 2

Preparation of Phenylhydroquinone in a Slurry Reactor

The previous example was repeated with invention catalyst employing the following procedure:

To a four-neck round bottom flask fitted with a mechanical stirrer, condenser, thermometer and tube for subsurface nitrogen addition were added 100 g biphenyl, 20.0 g cyclohexylhydroquinone and 2.0 g of a catalyst containing 5 wt % palladium and 1.5 wt % copper on carbon. The reaction mixture was heated to 250° C. with 0.5 SCFH subsurface addition of nitrogen and was stirred at 250° C. for 24 hours. The reaction mixture was then cooled to 150° C. and the catalyst removed by filtration through a sintered glass funnel. The catalyst can be recycled back for another run without further purification or treatment. The product filtrate analyzed by gas chromatography contained the following:

82.4 wt % phenyl hydroquinone,
8.3 wt % cyclohexyl hydroquinone,
0.7 wt % 2-phenylphenol,
2.0 wt % 3-phenylphenol, and
2.4 wt % hydroxydibenzofuran.

The phenylhydroquinone can be isolated in high yield and in pure form by vacuum distillation (the boiling point of phenylhydroquinone at 2.0 mm is 187° C.).

EXAMPLE 3

Dehydrogenation of Substituted Cyclohexylhydroquinones With the Catalyst of the Invention A variety of substituted cyclohexylhydroquinones of the formula

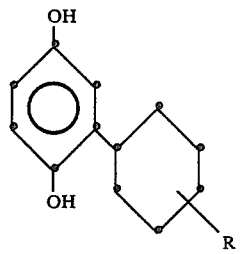

wherein R is —H, —CH₃, —C₆H₅, —OCH₃ and —O-CO—CH₃ (—OAc) were dehydrogenated to the corresponding substituted phenylhydroquinones employing the procedure set forth in Example I. The catalyst employed was 5 wt % Pd and 1.5 wt % Cu on carbon. The reaction was conducted at 250° C. with biphenyl as a solvent. The results of the experiments are set forth in Table 2.

TABLE 2
Dehydrogenation of Substituted Cyclohexylhydroquinones With Invention Catalyst

| R | Conversion (%) | Selectivity (%) |
|---|---|---|
| —H | 88 | 90 |
| p-CH₃ | 90 | 92 |
| p-C₆H₅ | 95 | 92 |
| p-OCH₃ | 90 | 90 |
| p-OAc | 75 | 90 |

The results of these experiments demonstrate that the invention method employing Pd-Cu on carbon support is effective for the conversion of a variety of substituted cyclohexylhydroquinones to produce a high yield of the corresponding substituted phenylhydroquinones. Selectivities to the desired phenylhyroquinone in all cases were 90% or greater, with conversions of at least 75%. It is especially noteworthy that essentially no hydrogenolysis occurred in any of these dehydrogenation reactions.

EXAMPLE 4

Comparison of Invention Catalyst with Other Catalysts

A series of experiments were carried out to compare the conversion of cyclohexylhydroquinone to phenylhydroquinone employing the palladium-copper on carbon catalyst of this invention, and employing prior art dehydrogenation catalysts. The experiments were all run at 250° C. in biphenyl as a solvent employing the procedure set forth in Example I.

The results of the experiments are set forth in Table 3.

TABLE 3

Comparison of Invention Catalyst with Prior Art Catalysts for the Dehydrogenation of Cyclohexylhydroquinone

| Catalyst | Conversion (%) | Selectivity (%) |
|---|---|---|
| 5% Pd/carbon | 100 | 4 |
| 5% Pt/carbon | 99 | 20 |
| 8% Pd, 2% Pt/carbon | 95 | 42 |
| 5% Rh/carbon | 37 | 69 |
| 5% Pd, 1.5% Cu/carbon | 88 | 90 |
| 5% Pd, 0.8% Ag/carbon | 72 | 57 |
| 5% Pd, 2.5% Cu/Al$_2$O$_3$ | 20 | 65 |
| 5% Pd, 2.5% Cu/SiO$_2$ | 12 | 82 |
| 5% Pd, 2.5% Cu/carbon | 43 | 99 |

Several prior art catalysts (e.g., Pd/C, Pt/C and Pd-Pt/C) give high levels of cyclohexylhydroquinone conversion, but selectivities to the desired product, phenylhydroquinone, are quite poor. Similarly, other prior art catalyst systems suffer from either low convesion levels, or poor selectivity, or both. Only invention catalyst containing Pd and Cu on carbon support are capable of giving yields of desired product.

EXAMPLE 5

Selective Dehydrogenation of Substituted Ethyl Benzenes to the Corresponding Styrenes with the Catalyst of the Invention A series of substituted ethyl benzenes was dehydrogenated to the corresponding styrenes according to the following chemical reaction:

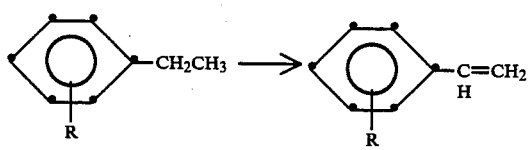

wherein R is —H, p—OH, p—OCH$_3$ and m—OCH$_3$.

These reactions were all carried out at 200° C. in 100 g biphenyl solvent in the apparatus described in Example I with 2 g of 5 wt % Pd and 2.5 wt % Cu on carbon as the catalyst and 20 g of ethyl benzene substrate. The results of these experiments are set forth in Table 4.

TABLE 4

Selective Dehydrogenation of Substituted Ethyl Benzenes

| R | Conversion (%) | Selectivity (%) |
|---|---|---|
| —H | 95 | 92 |
| p-OH | 97 | 90 |
| p-OCH$_3$ | 92 | 91 |
| m-OCH$_3$ | 90 | 92 |

In all cases, good yields (greater than 90% conversion and 90% selectivity) were obtained with a variety of substituted ethyl benzenes, thereby selectively producing a variety of substituted styrenes in high yield.

EXAMPLE 6

Selective Dehydrogenation of Substituted 1,2-diphenylethanes to the Corresponding Stilbenes A series of substituted 1,2-diphenylethanes were dehydrogenated to the corresponding stilbenes according to the following reaction.

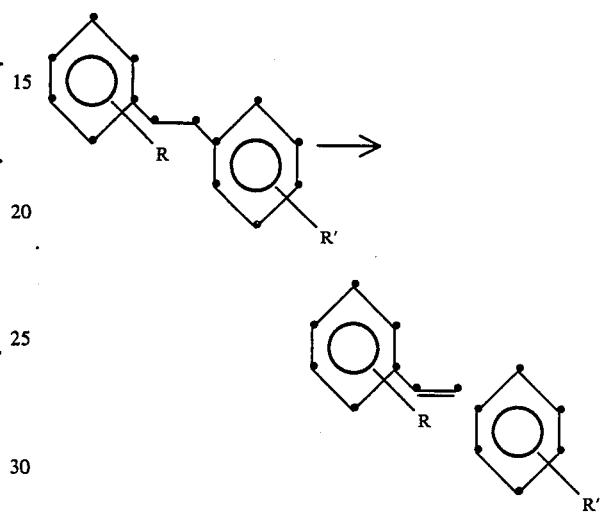

wherein each of R or R' is independently —H, p—OH, p—OCH$_3$ and p—COOCH$_3$.

These reactions were all conducted at 250° C. in the presence of 2 g of a 5 wt % Pd, 2.5 wt % Cu on carbon catalyst and 100 g biphenyl as a solvent, with 20 g of 1,2-diphenyl ethane substrate. The results of the experiments are set forth in Table 5.

TABLE 5

Selective Dehydrogenation of Substituted 1,2-Diphenylethanes

| R | R' | Conversion (%) | Selectivity (%) |
|---|---|---|---|
| —H | —H | 92 | 96 |
| p-OH | —H | 90 | 92 |
| p-OCH$_3$ | p-OH | 95 | 90 |
| p-OH | p-OH | 88 | 86 |
| p-COOCH$_3$ | p-COOCH$_3$ | 82 | 90 |

The results demonstrate that the invention Pd-Cu on carbon catalyst is effective for the selective dehydrogenation of diphenylethanes to produce stilbenes.

EXAMPLE 7

Dehydrogenation of n-Butane

The dehydrogenation of n-butane was conducted in the gas phase at 180° C. and 280° C. using a 8 wt % Pd, 2.5 wt % Cu on carbon catalyst. 3.8 g of the catalyst in powder form were placed in a plug flow microreactor and heated to reaction temperature in a flow of nitrogen gas. Once the reaction temperature was achieved, n-butane was fed to the catalyst bed at 170 SCCM and the amount of the products obtained at the two temperatures were monitored by gas chromatography. The results of these experiments are set forth in Table 6.

TABLE 6
Dehydrogenation of n-butane at Different Temperatures

| Temp. (°C.) | Products (mole %) | | | | | |
|---|---|---|---|---|---|---|
| | $CH_4$ | i-butane | 1-butene | c-butene | t-butene | 1,3-butadiene |
| 180 | 0.21 | 0.22 | 0.00 | 0.20 | 0.36 | 0.00 |
| 280 | 0.01 | 0.14 | 0.14 | 0.39 | 0.24 | 0.08 |

These results demonstrate that the invention Pd-Cu on carbon catalyst is effective for the dehydrogenation of saturated hydrocarbons such as butane, to produce unsaturated compounds. Note that at low reaction temperatures, high selectivity to the internal alkene, 2-butene, is obtained.

The invention now being fully described, it will be apparent to one of ordinary skill in the art that many changes and modifications can be made thereto without departing from the spirit or scope of the invention as set forth herein.

We claim:

1. A method for the selective dehydrogenation of a compound to produce an aromatic compounds or an acyclic olefin, said method, comprising dehydrogenating a compound of the formula

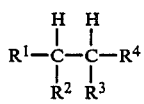

wherein each of $R^1$, $R^2$, $R^3$ and $R^4$ is independently selected from the group consisting of H, ($C_1$-$C_{20}$) alkyl, ($C_3$-$C_{20}$) cycloalkyl, ($C_6$-$C_{20}$) aryl, ($C_7$-$C_{20}$) alkylaryl, and ($C_7$-$C_{20}$) aralkyl groups, and substituted ($C_1$-$C_{20}$) alkyl, ($C_3$-$C_{20}$) cycloalkyl and ($C_6$-$C_{20}$) aryl, ($C_7$-$C_{20}$) alkylaryl and ($C_7$-$C_{20}$) aralkyl; each such group optionally substituted with —OR, wherein R is $R^1$, $R^2$, $R^3$ or $R^4$; and wherein $R^1$ and $R^2$ or $R^3$ and $R^4$ may be joined as part of a ring structure, at a dehydrogenation temperature in the presence of a catalyst comprising about 0.01 wt %–19.9 wt % Pd, and about 0.01 wt %–19.9 wt % Cu on a carbon support, wherein the total amount of (Pd+Cu) on the support is about 0.02 wt % to 20 wt %, the weight ratio of Pd:Cu is about 1:1 to 10:1, and the carbon support has a surface area of at least about 100 $m^2$/g and is essentially free of reactive sulfur.

2. The method of claim 1, wherein the dehydrogenating step is conducted in the presence of a catalyst consisting essentially of about 0.01 wt %–19.9 wt % Pd and about 0.01 wt %–19.9 wt % Cu on a carbon support, wherein the total amount of (Pd+Cu) on the support is about 0.02 wt % to 20 wt %, the weight ratio of Pd:Cu is about 1:1 to 10:1 and the carbon support has a surface area of at least about 100 $m^2$/g and is essentially free of reactive sulfur.

3. The method according to claim 1, wherein the palladium:copper ratio is about 3.0:1 to 4.0:1.

4. The method according to claim 1, wherein the dehydrogenating temperature is about 100° C. to 400° C.

5. The method according to claim 1, wherein the dehydrogenation is conducted in the presence of a reaction solvent.

6. The method according to claim 5, wherein the reaction solvent is selected from the group consisting of biphenyl, naphthalene, diphenyl ether, tetralin, durene and prehnitene.

7. The method according to claim 6, wherein the solvent is biphenyl.

8. The method according to claim 1, further comprising constantly removing hydrogen gas produced in the dehydrogenation step.

9. The method according to claim 8, wherein the hydrogen gas is removed by circulating an inert gas.

10. The method according to claim 8 wherein the hydrogen is removed by reaction with controlled levels of oxygen added to the dehydrogenation reaction zone.

11. The method according to claim 1 wherein the compound to be dehydrogenated is a straight chain alkane having 2 up to 20 carbon atoms.

12. The method according to claim 11 wherein the compound to be dehydrogenated is selected from the group consisting of:
propane,
butane,
pentane,
hexane,
heptane,
octane,
nonane, and
decane.

13. The method according to claim 11 wherein the compound to be dehydrogenated is selected from the group consisting of propane and butane.

14. The method according to claim 1 wherein the compound to be dehydrogenated is a branched chain alkane having 4 up to 20 carbon atoms.

15. The method according to claim 14 wherein the compound to be dehydrogenated is selected from the group consisting of branched chain alkanes having 4 up to 12 carbon atoms.

16. The method of according to claim 1 wherein the compound to be dehydrogenated is an alkyl aromatic compound of the formula

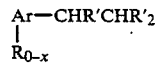

wherein each R is independently selected from the group consisting of
—OZ, wherein Z=H,
$C_1$-$C_{20}$ alkyl,
$C_3$-$C_{20}$ cycloalkyl,
$C_4$-$C_{20}$ aromatic or heteroaromatic moiety,

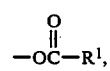

wherein $R^1$=$C_1$-$C_{20}$ alkyl, or $C_3$-$C_{20}$ cycloalkyl;

wherein Y=H
$C_1$-$C_{20}$ alkyl, or
$C_3$-$C_{20}$ cycloalkyl;

wherein Y is as defined above,
—SO$_y$Z', wherein
Z' is C$_1$–C$_{20}$ alkyl or C$_2$–C$_{20}$ cycloalkyl;
and y=1 or 2;
wherein each R' is independently H, C$_1$–C$_{20}$ alkyl, C$_3$–C$_{20}$ cycloalkyl, C$_4$–C$_{20}$ aromatic or heteroaromatic moiety;
wherein Ar is an aromatic moiety having 6 up to 14 carbon atoms;
wherein x is 4 when Ar has 6 carbons, x is 6 when Ar has 10 carbons and x is 8 when Ar is 14.

17. The method according to claim 16 wherein the compound to be dehydrogenated is selected from the group consisting of:
ethylbenzene,
p-hydroxy ethylbenzene,
p-methoxy ethylbenzene, and
m-methoxy ethylbenzene.

18. The method according to claim 1 wherein the compound to be dehydrogenated is a 1,2-diaryl ethane of the formula:

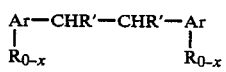

wherein each R is independently selected from the group consisting of
—OZ, wherein Z=H,
C$_1$–C$_{20}$ alkyl,
C$_3$–C$_{20}$ cycloalkyl,
C$_4$–C$_{20}$ aromatic or heteroaromatic moiety,

wherein R$^1$=C$_1$–C$_{20}$ alkyl, or C$_3$–C$_{20}$ cycloalkyl;

wherein Y=H
C$_1$–C$_{20}$ alkyl, or
C$_3$–C$_{20}$ cycloalkyl;

wherein Y is as defined above,
—SO$_y$Z', wherein
Z' is C$_1$–C$_{20}$ alkyl or C$_2$–C$_{20}$ cycloalkyl;
and y=1 or 2;
wherein each R' is independently H, C$_1$–C$_{20}$ alkyl, C$_3$–C$_{20}$ cycloalkyl, C$_4$–C$_{20}$ aromatic or heteroaromatic moiety;
wherein Ar is an aromatic moiety having 6 up to 14 carbon atoms;
wherein x is 4 when Ar has 6 carbons, x is 6 when Ar has 10 carbons and x is 8 when Ar is 14.

19. The method according to claim 18 wherein the compound to be dehydrogenated is selected from the group consisting of:
1,2-diphenylethane,
1-phenyl-2-p-hydroxyphenylethane,
1,2-bis(p-hydroxyphenyl)ethane,
1,2-bis(methyl-p-benzoate)ethane, and
1-p-hydroxyphenyl-2-p-methoxyphenyl ethane.

20. The method according to claim 1 wherein the compound to be dehydrogenated is a cyclohexyl hydroquinone compound of the formula:

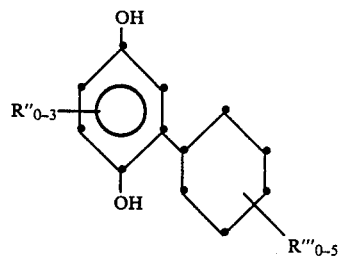

wherein each R" is independently C$_1$–C$_{20}$ alkyl, C$_3$–C$_{20}$ cycloalkyl, C$_4$–C$_{20}$ aromatic or heteroaromatic moiety; and wherein each R''' is independently
C$_1$–C$_{20}$ alkyl,
C$_3$–C$_{20}$ cycloalkyl,
C$_6$–C$_{12}$ aryl,
C$_7$–C$_{20}$ aralkyl or alkaryl,
—OZ, wherein Z=H,
C$_1$–C$_{20}$ alkyl,
C$_3$–C$_{20}$ cycloalkyl,
C$_4$–C$_{20}$ aromatic or heteroaromatic moiety,

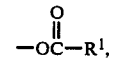

wherein R$^1$=C$_1$–C$_{20}$ alkyl, or C$_3$–C$_{20}$ cycloalkyl;

wherein Y=H,
C$_1$–C$_{20}$ alkyl, or
C$_3$–C$_{20}$ cycloalkyl;

wherein Y is as defined above,
—SO$_y$Z', wherein
Z' is C$_1$–C$_{20}$ alkyl, or C$_3$–C$_{20}$ cycloalkyl;
and y=1 or 2.

21. The method according to claim 1 wherein the compound to be dehydrogenated is selected from the group consisting of:
cyclohexylhydroquinone,
4-methylcyclohexyl hydroquinone,
4-phenylcyclohexyl hydroquinone,
4-methoxycyclohexyl hydroquinone, and
4-acetoxycyclohexyl hydroquinone.

22. The method according to claim 20, wherein the compound to be dehydrogenated is cyclohexylhydroquinone.

23. The method according to claim 22 wherein the phenylhydroquinone obtained in the dehydrogenation step is substantially free of hydrogenolysis by-products.

* * * * *